United States Patent

Yamamoto et al.

[11] Patent Number: 5,530,038
[45] Date of Patent: Jun. 25, 1996

[54] PRIMER COMPOSITION AND CURABLE COMPOSITION

[75] Inventors: Takashi Yamamoto; Weiping Zeng; Masami Arata; Tsuyoshi Banba, all of Moriyama; Harumi Tanaka, Hikone, all of Japan

[73] Assignee: Sun Medical Co., Ltd., Moriyama, Japan

[21] Appl. No.: 284,175

[22] Filed: Aug. 2, 1994

[30] Foreign Application Priority Data

| Aug. 2, 1993 | [JP] | Japan | 5-191476 |
| Aug. 2, 1993 | [JP] | Japan | 5-191477 |
| Aug. 2, 1993 | [JP] | Japan | 5-191478 |

[51] Int. Cl.$^6$ ............................ C08L 47/00; C08K 5/20
[52] U.S. Cl. .................. 523/116; 523/118; 524/240; 524/431; 524/493; 526/220; 526/227; 526/318.42; 526/320
[58] Field of Search .................... 523/116, 118; 524/240, 431, 493; 526/220, 227, 318.42, 320

[56] References Cited

U.S. PATENT DOCUMENTS

| 4,388,421 | 6/1983 | Suzuki et al. | 523/118 |
| 4,918,136 | 4/1990 | Kawaguchi et al. | 523/116 |
| 4,966,766 | 10/1990 | Atsata et al. | 424/78.05 |
| 5,154,762 | 10/1992 | Mitra et al. | 523/116 |
| 5,264,513 | 11/1993 | Ikemura et al. | 523/116 |
| 5,270,351 | 12/1993 | Bowen | 523/116 |

FOREIGN PATENT DOCUMENTS

| 0156605 | 8/1985 | Japan | 523/116 |
| 63-63605 | 3/1988 | Japan . | |
| 1230508 | 9/1989 | Japan . | |

*Primary Examiner*—Paul R. Michl
*Assistant Examiner*—Andrew E. C. Merriam
*Attorney, Agent, or Firm*—Sherman and Shalloway

[57] ABSTRACT

A curable composition comprising a polymerizable monomer having an acidic group in its molecule and an initiator. The composition has a viscosity in the range of from 100 to 30,000 cP at 37.5° C. and may have additionally contain other polymerizable monomer and/or a filler. The composition is applied to a tooth surface directly or after applying a primer composition. There is also provided the primer composition which comprises a polymerizable monomer having an acidic group and a solvent.

4 Claims, No Drawings

PRIMER COMPOSITION AND CURABLE COMPOSITION

DETAILED DESCRIPTION OF THE INVENTION

The present invention relates to a primer composition with which a tooth can be surface-treated by facile handling, and a curable composition which can be bonded to a tooth. More specifically, it relates to a primer composition and a curable composition which are advantageously used for restoring a tooth-surface coating material or restoring dental restorative resins such as a PMMA resin, resin cement and a composite resin.

An adhesive material for a tooth is desired not only to bond a tooth and a restorative material tightly and firmly but also to permit the completion of the restoration as easily and shortly as possible, since the restoration is conducted in the mouth.

For bonding a resin restorative material to a tooth firmly, there is employed one of the following three tooth-surface treating methods. That is, the first one of these methods is a total etching method in which enamel and dentin are first decalcified by simultaneously applying phosphoric acid or citric acid aqueous solution to surfaces of the enamel and dentin, then washed with water and dried. The second one is a total etching—dentin primer method in which a primer is applied to a dentin surface treated by the total etching method and then dried. The third one is an enamel etching—dentin primer method in which an enamel alone is etched and a primer is applied to remaining dentin.

The first total etching method is carried out through the steps of applying an etching agent, washing with water and drying, while it is effective as a bonding method since it is not a time-consuming method. Since, however, dental tubules are widely opened, a patient may have strong pains when an adhesive material is applied thereafter. Further, the bonding strength to dentin is lower than the bonding strength to enamel in many cases, and the interface between dentin and the adhesive material has a gap, which induces secondary caries or pulpitis. The second method is an improvement of the first method, in which, further, a primer is applied to dentin and dried. The first method is thereby improved to some extent. However, the second method requires an additional bonding procedure, which not only causes more pains on a patient but requires an additional time for the treatment. The third method is for decreasing pains to be caused on a patient, in which enamel alone is etched so that dental tubules are not opened, and a primer is applied. The purpose in this method is nearly accomplished, while the following problems still remain to be solved. That is, it is required to apply an etching agent only to a small and complicated enamel portion of a cavity where it is difficult to apply the etching agent distinctly, and the treatment takes time. That is because there is no primer which can treat both enamel and dentin and has high bonding strength.

On the other hand, for bonding a restorative material to a tooth strongly, it is considered essential to infiltrate an adhesive material into a tooth tissue sufficiently and cure it firmly. For sufficiently diffusing an adhesive material component into a tooth, a variety of diffusion-promoting monomers have been proposed, and dental adhesive compositions containing these monomers have been proposed. For the facile infiltration of an adhesive material, there have been proposed a method of etching and primer compositions for the surface treatment of a tooth. In general practice, these adhesive materials and primer compositions are arranged to have relatively low viscosities for the facile infiltration into a tooth tissue.

Further, as a material with which an adhesive interface is filled without forming any gap, JP-A-63-162705 discloses a filler having a high viscosity as compared with an adhesive material (called a low-viscosity filler or a low-viscosity material). The low-viscosity filler has a high viscosity and sticking nature, and it is therefore effective for improving the full contact in the adhesion interface, while the degree of filtration thereof into a tooth is low so that its adhesion to the tooth is poor. It is therefore used in combination with a primer or an adhesive material.

In prior art practice, the following has been considered the most preferred technique for bonding a restorative material to a tooth firmly without forming any gap. That is, a tooth surface is treated by etching and/or with a primer, an adhesive material is applied to the tooth surface and cured, the tooth surface is coated with a low-viscosity filler and then a restorative filler such as a composite resin is filled in. However, the dental treatment therefor takes a very long period of time so that a patient is forced to suffer much pains, and it is also a time-consuming treatment on a dentist's part. It therefore cannot be said that the above practice is preferable.

For adhesion performance, many adhesive materials and bonding methods have been proposed and improved. Experimental adhesion performances in these proposals are excellent, while these proposals are not satisfactory since no sufficient performances are exhibited when they are actually clinically evaluated. It is assumed that the above unsatisfactory performances can be explained on the basis of a difference between an adhesion surface used in an experiment for adhesion performance and an actual adhesion surface in the mouth. It is pointed out, in particular, that a dry state differs between the above adhesion surfaces.

The prior art practice therefore has the following serious problems. A dentist and a patient are forced to have efforts or suffer much pains for a long period of time for bonding a restorative material to a tooth firmly without forming any gap, and further, an adhesive material cannot exhibit adequate adhesion performance in the mouth where a sufficient dry state cannot be maintained.

It is therefore an object of the present invention to provide a primer composition or a tooth surface treating agent with which a tooth can be surface-treated by facile handling.

It is another object of the present invention to provide a primer composition with which enamel and dentin can be surface-treated at the same time and procedures such as washing with water are not required, so that the time required for the treatment by a dentist can be decreased and that pains caused on a patient can be alleviated.

It is further another object of the present invention to provide a curable composition which can be bonded to a tooth, dentin in particular, by facile handling and without forming any gap even under wet conditions.

It is still further another object of the present invention to provide a curable composition which has adhesion properties to dentin not treated with acid etching or a primer and has a high viscosity and sticking nature as an adhesive so that, advantageously, no gap is formed in an adhesion interface, and which therefore can be bonded to dentin by facile handling.

Other objects and advantages of the present invention will be apparent from the following description.

The above objects and advantages of the present invention will be achieved by the primer composition and the curable composition of the present invention which will be detailed hereinafter.

First, the curable composition will be detailed below.

The curable composition of the present invention comprises (A1) (a) a polymerizable monomer having an acidic group in its molecule, (b) a polymerizable monomer having a hydroxyl group in its molecule, and (c) a polymerization initiator, wherein:

on the basis of a total amount of components (a), (b) and (c), the amount of the component (a) is 1 to 50% by weight, the amount of the component (b) is 1 to 98.99% by weight and the amount of the component (c) is 0.01 to 50% by weight, (B1) the curable composition having a viscosity in the range of from 100 to 30,000 cp when measured at 37.5° C.

The curable composition of the present invention has all of wettability to a tooth surface, reactivity to a tooth and infiltration properties to a tooth at the same time and can be bonded to a living hard tissue without forming any gap by facile handling.

When the curable composition of the present invention is applied to a tooth, dentin in particular, it is preferred to bring it into contact with a wet tooth in view of safety to dental pulp. In some use, a tooth may be surface-treated with an etching agent such as a phosphoric acid aqueous solution which may contain a metal salt, a citric acid aqueous solution or an EDTA aqueous solution before the curable composition of the present invention is applied.

The (a) polymerizable monomer having an acidic group in its molecule, used in the curable composition of the present invention, has a polymerizable group selected from radical-polymerizable unsaturated groups such as a (meth)acryloyl group, a styryl group, a vinyl group and an allyl group. The polymerizable monomer (a) is a monomer of which the molecule contains at least one member selected from the above polymerizable groups (a polymerizable group in polymerizable monomers to be described hereinafter should be all interpreted in this sense).

In the curable composition of the present invention, the component (a) is a polymerizable monomer containing an acidic group in its molecule. The acidic group in the above polymerizable monomer includes a carboxylic acid group, a phosphoric acid group, a thiophosphoric acid group, a sulfonic acid group and a sulfinic acid group. The component (a) preferably contains at least one of the above acidic groups.

Of the polymerizable monomers used as the component (a), the polymerizable monomer having at least one carboxyl group in its molecule includes monocarboxylic acid, dicarboxylic acid, tricarboxylic acid, tetracarboxylic acid and derivatives of these such as (meth)acrylic acid, maleic acid, p-vinylbenzoic acid, 11-(meth)acryloyloxy-1,1-undecanedicarboxylic acid (where it is methacrylate: MAC-10), 1,4-di(meth)acryloyloxyethylpyromellitic acid, 6-(meth)acryloyloxyethylnaphthalene- 1,2,6-tricarboxylic acid, 4-(meth)acryloyloxymethyltrimellitic acid and an anhydride thereof, 4-(meth)acryloyloxyethyltrimellitic acid (where it is methacrylate: 4-MET) and an anhydride thereof (where it is methacrylate: 4-META), 4-(meth)acryloyloxybutyltrimellitic acid and an anhydride thereof, 4-(2-hydroxy-3-(meth)acryloyloxy)butyltrimellitic acid and an anhydride thereof, 2,3-bis(3,4-dicarboxybenzoyloxy)propyl (meth)acrylate, N,O-di(meth)acryloyloxytyrosine, O-(meth)acryloyloxytyrosine, N-(meth)acryloyloxytyrosine, N-(meth)acryloyloxyphenylalanine, N-(meth)acryloyl-p-aminobenzoic acid, N-(meth)acryloyl-O-aminobenzoic acid, N-(meth)acryloyl-5-aminosalicylic acid (where it is methacrylate: 5-MASA), N-(meth)acryloyl-4-aminosalicylic acid, 2-, 3- or 4-(meth)acryloyloxybenzoic acid, an adduct of 2-hydroxyethyl (meth)acrylate with pyromellitic dianhydride (where it is methacrylate: PMDM), an addition reaction product of 2-hydroxyethyl (meth)acrylate with maleic anhydride or 3,3',4,4'-benzophenonetetracarboxylic dianhydride (where it is methacrylate: BTDA) or 3,3',4,4'-biphenyltetracarboxylic dianhydride, an adduct of 2-(3,4-dicarboxybenzoyloxy) 1,3-di(meth)acryloyloxypropane, N-phenylglycine or N-tolylglycine with glycidyl (meth)acrylate, 4-((2-hydroxy-3-(meth)acryloyloxypropyl)amino)phthalic acid, and 3- or 4-(N-methyl-N-( 2-hydroxy-3-(meth)acryloyloxypropyl)amino)phthalic acid. Preferred are MAC-10, 4-MET and 5-MASA. The above polymerizable monomers having a carboxyl group may be used alone or in combination.

Of the polymerizable monomers used as the component (a), the polymerizable monomer having at least one phosphoric acid group in its molecule includes 2-(meth)acryloyloxyethyl acidophosphate, 2- and 3-(meth)acryloyloxypropyl acidophosphate, 4-(meth)acryloyloxybutyl acidophosphate, 6-(meth)acryloyloxyhexyl acidophosphate, 8-(meth)acryloyloxyoctyl acidophosphate, 10-(meth)acryloyloxydecyl acidophosphate, 12-(meth)acryloyloxydodecyl acidophosphate, bis{2-(meth)acryloyloxyethyl}acidophosphate, bis{2- or 3-(meth)acryloyloxypropyl}acidophosphate, 2-(meth)acryloyloxyethylphenyl acidophosphate, and 2-(meth)acryloyloxyethyl p-methoxyphenyl acidophosphate. The phosphoric acid group in these compounds may be replaced with a thiophosphoric acid group. Preferred are 2-(meth)acryloyloxyethylphenyl acidophosphate and 10-(meth)acryloyloxydecyl acidophosphate. The above polymerizable monomers having a phosphoric acid group may be used alone or in combination.

Of the polymerizable monomers used as the component (a), the polymerizable monomer having at least one sulfonic acid group in its molecule includes 2-sulfoethyl (meth)acrylate, 2- or 1-sulfo-1 or 2-propyl (meth)acrylate, 1- or 3-sulfo-2-butyl (meth)acrylate, 3-bromo-2-sulfo-2-propyl (meth)acrylate, 3-methoxy-1-sulfo-2-propyl (meth)acrylate, and 1,1-dimethyl-2-sulfoethyl (meth)acrylamide. Preferred is 1,1-dimethyl-2-sulfoethyl (meth)acrylamide. The above polymerizable monomers having a sulfonic acid may be used alone or in combination.

All the above polymerizable monomers included in the component (a) may be used alone or in combination.

In the curable composition of the present invention, the component (b) is a polymerizable monomer containing a hydroxyl group in its molecule. Further, this polymerizable monomer containing a hydroxyl group may further contain any one of functional groups such as a carboxyl group, a phosphoric acid group, a sulfonic acid group, a hydroxyl group, an amino group and a glycidyl group.

Of the polymerizable monomers used as the component (b), the polymerizable monomer having a (meth)acryloyl group includes hydroxyl group-containing (meth)acrylates such as 2-hydroxyethyl (meth)acrylate, 2- or 3-hydroxypropyl (meth)acrylate, 4-hydroxybutyl (meth)acrylate, 5-hydroxypentyl (meth)acrylate, 6-hydroxyhexyl (meth)acrylate, 10-hydroxydecyl (meth)acrylate, 1,2- or 1,3- and 2,3-dihydroxypropane (meth)acrylate, diethylene glycol mono(meth)acrylate, triethylene glycol mono(meth)acrylate, pentaethylene glycol mono(meth)acrylate, polyethylene glycol mono(meth)acrylate and dipropylene glycol mono(meth)acrylate; hydroxyl group-containing (meth)acrylamides such as methylol(meth)acrylamide, N-(meth)acryloyl- 2,3-dihydroxypropylamine and N-(meth)acryloyl- 1,3-dihydroxypropylamine; and adducts of glycidyl methacrylate with aliphatic or aromatic polyols (including phenol) such as 2-hydroxy-3-phenoxypropyl (meth)acrylate (where it is methacrylate: HPPM), 2-hydroxy-3-naphthoxypropyl (meth)acrylate (where it is methacrylate: HNPM) and an addition reaction product of 1 mol of bisphenol A with 2 mol of glycidyl (meth)acrylate (where it is methacrylate: GMA) (where the addition reaction product is methacrylate: Bis-GMA). The above polymerizable monomers may be used alone or in combination.

Of the above polymerizable monomers as the component (b), it is particularly preferred to use monomers whose solubility in water is at least 0.5 g/100 cc. It is assumed that this monomer plays the role of allowing the curable composition to easily infiltrate a tooth tissue even when the curable composition is applied to an adhesion interface having a high water content. The solubility used in the present invention is defined as follows. That is, 0.5 part by weight of a monofunctional (meth)acrylate monomer having at least one hydroxyl group in its molecule is added to 100 parts by weight of water having a temperature of 25° C. and the mixture is shaken for 10 minutes. Then, the mixture is allowed to stand at 25° C. for 10 minutes and then visually evaluated. When the mixture solution has separated phases or is a turbid solution, the solubility of the above (meth)acrylate in water is taken as less than 0.5 g/100 cc. When the mixture is a transparent solution, the solubility is taken as at least 0.5 g/100 cc.

The component (b) whose solubility in water is at least 0.5 g/100 cc includes 2-hydroxyethyl (meth)acrylate, 2- or 3-hydroxypropyl (meth)acrylate, 4-hydroxybutyl (meth)acrylate, 5-hydroxypentyl (meth)acrylate, 6-hydroxyhexyl (meth)acrylate, 10-hydroxydecyl (meth)acrylate, diethylene glycol mono(meth)acrylate, triethylene glycol mono(meth)acrylate, tetraethylene glycol mono(meth)acrylate, polyethylene glycol mono(meth)acrylate, dipropylene glycol mono(meth)acrylate, tripropylene glycol mono(meth)acrylate, tetrapropylene glycol mono(meth)acrylate, polypropylene glycol mono(meth)acrylate, 1,3- or 2,3-dihydroxypropyl (meth)acrylate, N-(meth)acryloyl-2,3-dihydroxylpropylamine and N-(meth)acryloyl-1,3-dihydroxypropylamine. These monomers may be used alone or in combination. Of these polymerizable monomers, 2-hydroxyethyl (meth)acrylate (where it is methacrylate: HEMA) is particularly preferred, and it is preferred to incorporate 40 to 98.99 parts by weight, per 100 parts by weight of the total amount of the components (a), (b) and (c), of 2-hydroxyethyl (meth)acrylate as part of the component (b).

In the curable composition of the present invention, the component (c) is a polymerization initiator. This polymerization initiator includes organic peroxide, inorganic peroxide, alkylborane, partially oxidized alkylborane, an α-diketone compound, an organic amine compound, organic sulfinic acid, organic sulfinic acid salt, an inorganic sulfur compound and barbituric acids. The above polymerization initiators may be used alone or in combination. The above polymerization initiators can be grouped into a type for room temperature chemical polymerization, a type for photopolymerization and a dual type for a combination of the above polymerizations. The peroxide (polymerization initiator) which is used as a type for room temperature chemical polymerization includes organic peroxides such as diacetyl peroxide, dipropyl peroxide, dibutyl peroxide, dicapryl peroxide, dilauryl peroxide, benzoyl peroxide (BPO), p,p'-dichlorobenzoyl peroxide, p,p'-dimethoxybenzoyl peroxide, p,p'-dimethylbenzoyl peroxide and p,p'-dinitrobenzoyl peroxide and inorganic peroxides such as ammonium persulfate, potassium persulfate, potassium chlorate, potassium bromate and potassium perphosphate. Of these, BPO is preferred.

The polymerization initiator which is used as a type for the photopolymerization is a polymerization initiator with which the polymerization can be carried out by irradiating the composition with ultraviolet light or visible light. The polymerization initiator used for the above photopolymerization is not specially limited. The above polymerization initiator includes ultraviolet light or visible light sensitizers such as α-diketone compounds including benzil, 4,4'-dichlorobenzil, benzoin, benzoin methyl ether, benzoin ethyl ether, benzoin isopropyl ether, benzophenone, 9,10-anthraquinone, diacetyl and d,l-camphorquinone (CQ).

When the polymerization is carried out in the presence of a polymerization initiator which is a type for room temperature chemical polymerization or photopolymerization, a reducing compound may be used in combination. The organic reducing compound includes aromatic amines such as N,N-dimethylaniline, N,N-dimethyl p-toluidine (DMPT), N,N-diethyl p-toluidine, N,N-diethanol p-toluidine (DEPT), N,N-dimethyl p-tertbutylaniline. N,N-dimethylanisidine, N,N-dimethyl p-chloroaniline, N,N-dimethylaminoethyl (meth)acrylate. N,N-diethylaminoethyl (meth)acrylate, N,N-dimethylaminobenzoic acid and alkyl ester thereof. N,N-diethylaminobenzoic acid (DEABA) and alkyl ester thereof and N,N-dimethylaminobenzaldehyde (DMABAd); N-phenylglycine (NPG), N-tolylglycine (NTG) and N,N-(3-methacryloyloxy- 2-hydroxypropyl)phenylglycine (NPG-GMA).

Of the above reducing compounds, preferred are DMPT, DEPT, DEABA, DMABAd, NPG and NTG.

Further, for reliably curing the curable composition of the present invention and improving the curable composition of the present invention in adhesion to a tooth, it is preferred to incorporate at least one of amine compounds of the formula (I),

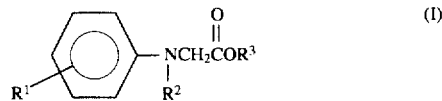

wherein each of $R^1$ and $R^2$ is independently a hydrogen atom or an alkyl group which may contain a functional group or a substituent, and $R^3$ is a hydrogen atom or metal, and of the formula (II),

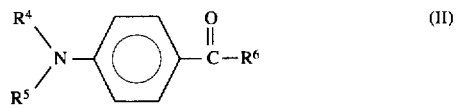

wherein each of $R^4$ and $R^5$ is independently a hydrogen atom or an alkyl group, and $R^6$ is a hydrogen atom, an alkyl group which may contain a functional group or a substituent or an alkoxyl group which may contain a functional group or a substituent.

The amine compound coming under the formula (I) includes NPG, NTG and NPG-GMA which are already described. NPG is particularly preferred. The amine compound of the formula (II) includes, in addition to N,N- dimethylaminobenzoic acid and alkyl ester thereof and N,N-diethylaminobenzoic acid (DEABA) and alkyl ester thereof, which are already described, aliphatic alkylaminobenzoic acids and alkyl esters thereof typified by N,N-dipropylaminobenzoic acid and alkyl ester thereof, N-isopropylaminobenzoic acid and alkyl ester thereof and N-isopropyl-N-methylaminobenzoic acid and alkyl ester thereof; aliphatic alkylaminobenzoaldehydes typified by DMABAd, N,N-diethylaminobenzoaldehyde, N,N-dipropylaminobenzoaldehyde and N-isopropyl-N-methylaminobenzaldehyde; aliphatic alkylaminoacetylbenzenes typified by N,N-dimethylaminoacetylbenzene, N,N-diethylaminoacetylbenzene., N,N-dipropylaminoacetylbenzene, N-isopropylaminoacetylbenzene and N-isopropyl-N-methylaminoacetylbenzene and aliphatic alkylaminoacylbenzenes. These amine compounds may be used alone or in combination.

In addition to the above compounds, the reducing compound includes aromatic sulfinic acids such as benzenesulfinic acid, o-toluenesulfinic acid, ethylbenzenesulfinic acid, decylbenzenesulfinic acid, dodecylbenzenesulfinic acid, chlorobenzenesulfinic acid and naphthalenesulfinic acid and salts thereof.

The inorganic reducing compound is preferably selected from sulfur-containing, reducing inorganic compounds. These compounds are preferably reducing inorganic compounds used as redox initiators which can be used for polymerizing a radical-polymerizable monomer in a solvent such as water or a water-containing solvent. Examples thereof include sulfurous acid, bisulfurous acid, metasulfurous acid, metabisulfurous acid, pyrosulfurous acid, thiosulfurous acid, dithionous acid, dithionic acid, hyposulfurous acid, hydrosulfurous acid and salts of these. Of these, sulfites are preferred, and particularly preferred are sodium sulfite, potassium sulfite, sodium hydrogensulfite and potassium hydrogensulfite. These reducing inorganic compounds may be used alone or in combination.

Per 100 parts by weight of the components (a), (b) and (c), the curable composition of the present invention contains 1 to 50 parts by weight of the component (a), 1 to 98.99 parts by weight of the component (b) and 0.01 to 50 parts by weight of the component (c). Preferably, the curable composition contains 1 to 30 parts by weight of the component (a), 3 to 90 parts by weight of the component (b) and 0.1 to 20 parts by weight of the component (c).

The curable composition of the present invention may further contain at least one of (d) other polymerizable monomer copolymerizable with at least one of the above components (a) and (b), and (e) at least one member selected from the group consisting of an organic filler, an inorganic filler and an organic composite filler.

The curable composition of the present invention, which contains none of the above components (d) and (e), will be referred to as a first curable composition. The curable composition of the present invention, which contains the component (d) alone, will be referred to as a second curable composition. The component (d) is a polymerizable monomer which is copolymerizable with at least one of the components (a) and (b). This polymerizable monomer includes monomers having radical-polymerizable unsaturated group such as a (meth)acryloyl group, a styryl group, a vinyl group or an allyl group. The polymerizable monomer can be a monomer whose molecule has at least one group selected from the above polymerizable groups. The above polymerizable monomer may contain, in its molecule, a functional group such as a carboxyl group, a phosphoric acid group, a sulfonic acid group, a hydroxyl group, an amino group or a glycidyl group.

The polymerizable monomer used as the component (d) includes aliphatic esters of (meth)acrylic acids such as methyl (meth)acrylate, ethyl (meth)acrylate, propyl (meth)acrylate, butyl (meth)acrylate, neopentyl glycol di(meth)acrylate and trimethylolpropane tri(meth)acrylate; polyethylene glycol di(meth)acrylates such as ethylene glycol di(meth)acrylate, diethylene glycol di(meth)acrylate, triethylene glycol di(meth)acrylate, pentaethylene glycol di(meth)acrylate, nonaethylene glycol di(meth)acrylate and tetradecaethylene glycol di(meth)acrylate; polypropylene glycol di(meth)acrylates such as propylene glycol di(meth)acrylate, dipropylene glycol di(meth)acrylate, tripropylene glycol di(meth)acrylate and nonapropylene glycol di(meth) acrylate; mono(meth)acrylates in which the (meth)acryloyl group of the above polyethylene glycol di(meth)acrylates or the above polypropylene glycol di(meth)acrylates is replaced with a methyl group or an ethyl group; (meth)acrylates having a urethane bond such as an adduct of 2-(meth)acryloyloxyethyl isocyanate, 2,2,4-trimethylhexamethylene diisocyanate or 1,3,5-trimethylhexamethylene diisocyanate with 2-hydroxyethyl (meth)acrylate; 2,2-bis(4-(meth)acryloyloxypolyethoxyphenyl)propanes obtained by forming an adduct of bisphenol A with oxyethylene and further condensing the adduct and (meth)acrylic acid; styrene derivatives such as styrene, 4-methylstyrene, 4-chloromethylstyrene and divinylbenzene; and vinyl acetate. These polymerizable monomers may be used alone or in combination.

The above various polymerizable monomers described as the component (d) may be used alone or in combination.

On the basis of the total amount of the components (a), (b) and (c), the second curable composition of the present invention contains 1 to 50% by weight of the component (a), 1 to 98.99% by weight of the component (b) and 0.01 to 50% by weight of the component (c). Further, the second curable composition of the present invention contains the component (d) in an amount of 3 to 50% by weight on the basis of the total amount of the components (a), (b), (c) and (d).

The first and second curable compositions of the present invention are required to have a viscosity in the range of from 100 to 30,000 cP, preferably 100 to 20,000 cP, more preferably 100 to 8,000 cP, when measured at 37.5° C. with a viscometer TYPE-EHD (supplied by TOKIMEC Co., Ltd). Having the viscosity in the above range, the first and second curable compositions exhibit excellent full contact and adhesion properties without forming any gap in an adhesion interface with a tooth.

The curable composition of the present invention, which further contains the component (e) alone, will be referred to as a third curable composition.

In the third curable composition of the present invention, the component (e) is at least one filler selected from an organic filler, an inorganic filler and an organic composite filler. The organic filler includes a powdered polymer filler obtained by milling a polymer or by dispersion polymerization, and a filler obtained by polymerizing a polymerizable monomer containing a crosslinking agent and milling the resultant polymer. The polymerizable monomer as a raw material for the above filler is not specially limited, while a polymer is preferably selected from homopolymers and copolymers from those polymerizable monomers described with regard to the components (b) and (d). The polymer includes polymethyl methacrylate (PMMA), polyethyl methacrylate, polypropyl methacrylate, polybutyl methacrylate (PBMA), polyvinyl acetate (PBAc), polyethylene glycol (PEG), polypropylene glycol (PPG) and polyvinyl alcohol (PVA).

The inorganic filler includes silica, silica alumina, alumina, alumina quartz, glass (including barium glass), titania, zirconia, calcium carbonate, kaolin, clay, mica, aluminum sulfate, barium sulfate, calcium carbonate, titanium oxide and calcium phosphate.

The organic composite filler includes fillers obtained by coating surfaces of the above inorganic fillers with polymerizable monomers by polymerization and then milling the coated fillers. Specifically, the organic composite filler includes a filler (TMPT.f) obtained by coating a fine silica powder or zirconium oxide of the above inorganic filler with a polymerizable monomer composed mainly of trimethylolpropane tri(meth)acrylate (TMPT) by polymerization.

When the curable composition of the present invention is used as a resin cement, particularly preferred as the component (e) is a filler which contains 40 to 80 parts by weight of a zirconium oxide filler having an average particle diameter of 0.05 to 10 μm, 10 to 30 parts by weight of a spherical silica filler having an average particle diameter of 1 to 10 μm and 10 to 30 parts by weight of an organic composite filler having an average particle diameter of 1 to 30 μm, preferably 5 to 30 μm. Further, as the above zirconium oxide filler, preferred is a filler which is obtained by coating zirconium oxide with a polymer soluble in the component (b), e.g., PMMA or polyvinyl acetate (PVAc), and which has an average particle diameter of 1 to 30 μm, particularly 5 to 30 μm.

In the third curable composition of the present invention, on the basis of the total amount of the components (a), (b) and (c), the amount of the component (a) is 1 to 50% by weight, the amount of the component (b) is 1 to 98.99% by weight, and the amount of the component (c) is 0.01 to 50% by weight. Further, on the basis of the total amount of the components (a), (b), (c) and (e), the amount of the component (e) is 15 to 85% by weight.

Further, the curable composition of the present invention may contain both the components (d) and (e). The curable composition of the present invention, which further contains both the components (d) and (e), will be referred to as a fourth curable composition of the present invention.

It should be understood that the explanations already given with regard to the components (d) and (e) for the second and third curable compositions can be directly applied to the components (d) and (e) for the fourth curable composition.

In the fourth curable composition of the present invention, on the basis of the total amount of the components (a), (b) and (c), the amount of the component (a) is 1 to 50% by weight, the amount of the component (b) is 1 to 98.99% by weight, and the amount of the component (c) is 0.01 to 50% by weight. Further, on the basis of the total amount of the components (a), (b), (c) and (d), the amount of the component (d) is 3 to 50% by weight, and on the basis of the total amount of the components (a), (b), (c), (d) and (e), the amount of the component (e) is 15 to 85% by weight.

Owing to the use of the component (e) in the third and fourth curable compositions of the present invention, the viscosity of these compositions can be easily changed, and these compositions can be adjusted to a viscosity in the range of from 100 to 30,000 cp when measured at 37.5° C. Since, however, the third and fourth curable compositions show handling properties different from those of the first and second curable compositions in some cases, the third and fourth curable compositions are preferably defined by the weight range of the component (e) rather than the viscosity.

In the first to fourth curable compositions of the present invention, the above components (a) to (e) may be mixed in advance and applied to a tooth. When a mixture of the above components might change in form and performance to impair the effects of the present invention because of storing it for a long period of time, each component may be separately stored. Or, these components may be divided to combinations as required, and stored, and these components may be mixed before use to prepare the curable composition.

The method for storing the curable compositions includes a method in which the above components are divided into two groups such as a mixture of the components (a/b(/d/e)) and the component (c) and a method in which the above components are divided into a mixture of the components (a/b(/d/e)) and a mixture of the components (b(/d/e)/c). These mixtures may be placed in separate containers and prepared as a kit for providing them as a commercial product. When the component (c) consists of two components, either BPO or CQ and an amine, the above components are divided into a mixture of the components (a/b/c (BPO or CQ)(/d/e)) and a mixture of the components (b(/d/e)/c(amine, e.g., N,N-dimethyl p-toluidine (to be abbreviated as DMPT))). Further, part or the whole of the component (c) may be contained in a tool to be used for applying a curable composition to a tooth surface, and in this case, the tool is brought into contact with the components (a), (b), (d) and (e) to prepare the curable composition immediately before use, and the curable composition is applied to a tooth surface. Although not specially limited, the tool used for applying the curable composition to a tooth surface preferably includes a brush, a ball or cloth of fiber, and a ball or piece of sponge.

That is, according to the present invention, there is provided a method of applying any one of the curable compositions, which comprises allowing a tool for applying a curable composition to a tooth surface to contain part or the whole of the component (c), then bringing the components (a), (b) and optionally (d) and a remaining component (c) if any into contact with the tool to prepare the curable composition on the tool, and applying the curable composition to a tooth surface immediately after the curable composition has been prepared.

In the above method, a time can be saved as compared with a method, for example, in which a curable composition is divided into two portions and stored in two containers and the two portions are mixed just before use. Further, the curable composition can be used economically by bringing a necessary amount of the curable composition into contact with the tool such as a sponge without using a mixing container. The curable composition of the present invention is so applied to a tooth surface and then a dental restorative resin is applied thereon, whereby the dental restoration can be advantageously conducted.

According to the present invention, for achieving the above objects, second, there is further provided a primer composition comprising (a) a polymerizable monomer having an acidic group in its molecule, and (f) a solvent selected from the group consisting of an organic solvent and an aqueous organic solvent.

The primer composition or tooth surface treating agent of the present invention can be used for treating a surface of enamel and dentin at the same time, and is suitable for applying an adhesive material to a tooth.

In the tooth surface treating agent of the present invention, the component (a) is a polymerizable monomer having an acidic group in its molecule. The polymerizable group of the above polymerizable monomer includes a radical-polymerizable unsaturated group having a (meth)acryloyl group, a styryl group, a vinyl group or an allyl group. The above polymerizable monomer can be a monomer whose molecule contains at least one group selected from these polymerizable groups (a polymerizable group in polymerizable monomers to be described hereinafter should be all interpreted in this sense). The polymerizable monomer having an acidic group in its molecule may contain any one of functional groups such as a carboxyl group, a phosphoric acid group, a sulfonic acid group, a hydroxyl group, an amino group and a glycidyl group.

The above polymerizable monomer as the component (a) includes those described with regard to the component (a) for the curable composition of the present invention.

In the tooth surface treating agent of the present invention, the component (f) is an organic solvent or an aqueous organic solvent. The organic solvent is selected from those which can uniformly dissolve or disperse the component (a) or a component (g) to be described later. Further, the organic solvent is preferably miscible with water. The organic solvent includes alcohols such as methanol, ethanol (EtOH) and propanol; ketones such as acetone and methyl ethyl ketone; ethers such as tetrahydrofuran; and amides such as N,N-dimethylformamide. In view of toxicity and stimulation to dental pulp, it is particularly preferred to use ethanol or acetone.

Further, the component (f) may contain water as described above. The water includes distilled water, ion-exchanged water and a physiological saline solution. Distilled water and ion-exchanged water are preferred. The organic solvent as the component (f) therefore may be used as a mixture thereof with water. In this case, particularly preferred is a mixture of water with ethanol or a mixture of water with acetone.

In the tooth surface treating agent of the present invention, per 100 parts by weight of the total amount of the components (a) and (f), the amount of the component (a) is 0.1 to 30 parts by weight, and the amount of the component (f) is 70 to 99.9 parts by weight. Preferably, the amount of the component (a) is 1 to 20 parts by weight, and the amount of the component (f) is 80 to 99 parts by weight.

In addition to the above components (a) and (f), the tooth surface treating agent of the present invention may further contain at least one member selected from the group consisting of (g) a polymerizable monomer copolymerizable with the above component (a), and (c) a polymerization initiator.

The above component (g) is a polymerizable monomer which is copolymerizable with the component (a). Although not specially limited, the above component (g) includes aliphatic acid esters of (meth)acrylic acid such as methyl (meth)acrylate, ethyl (meth)acrylate, propyl (meth)acrylate, butyl (meth)acrylate, neopentyl glycol di(meth)acrylate and trimethylolpropane tri(meth)acrylate; polyethylene glycol di(meth)acrylates such as ethylene glycol di(meth)acrylate, diethylene glycol di(meth)acrylate, triethylene glycol di(meth)acrylate, pentaethylene glycol di(meth)acrylate, nonaethylene glycol di(meth)acrylate and tetradecaethylene glycol di(meth)acrylate; polypropylene glycol di(meth)acrylates such as propylene glycol di(meth)acrylate, dipropylene glycol di(meth)acrylate, tripropylene glycol di(meth)acrylate and nonapropylene glycol di(meth)acrylate; mono(meth)acrylates in which the (meth)acryloyl group of the above polyethylene glycol di(meth)acrylates or the above polypropylene glycol di(meth)acrylates is replaced with a methyl group or an ethyl group; (meth)acrylates having a urethane bond such as an adduct of 2-(meth)acryloyloxyethyl isocyanate, 2,2,4-trimethylhexamethylene diisocyanate or 1,3,5-trimethylhexamethylene diisocyanate with 2-hydroxyethyl (meth)acrylate; 2,2-bis(4-(meth)acryloyloxypolyethoxyphenyl)propanes obtained by forming an adduct of bisphenol A with oxyethylene and further condensing the adduct and (meth)acrylic acid; styrene derivatives such as styrene, 4-methylstyrene, 4-chloromethylstyrene and divinylbenzene; and vinyl acetate. These polymerizable monomers may be used alone or in combination.

The component (g) is further selected from polymerizable monomers having a hydroxyl group in their molecules. These polymerizable monomers, as monomers having a (meth)acryloyl group, include hydroxyl group-containing (meth)acrylates such as 2-hydroxyethyl (meth)acrylate, 2- or 3-hydroxypropyl (meth)acrylate, 4-hydroxybutyl (meth)acrylate, 5-hydroxypentyl (meth)acrylate, 6-hydroxyhexyl (meth)acrylate, 10-hydroxydecyl (meth)acrylate, 1,2- or 1,3- and 2,3-dihydroxypropane (meth)acrylate, diethylene glycol mono(meth)acrylate, triethylene glycol mono(meth)acrylate, pentaethylene glycol mono(meth)acrylate, polyethylene glycol mono(meth)acrylate and dipropylene glycol mono(meth)acrylate; hydroxyl group-containing (meth)acrylamides such as methylol(meth)acrylamide, N-(meth)acryloyl- 2,3-dihydroxypropylamine and N-(meth)acryloyl- 1,3-dihydroxypropylamine; and adducts of glycidyl methacrylate with aliphatic or aromatic polyols (including phenol) such as 2-hydroxy-3-phenoxypropyl (meth)acrylate (where it is methacrylate: HPPM), 2-hydroxy-3-naphthoxypropyl (meth)acrylate (where it is methacrylate: HNPM) and an addition reaction product of 1 mol of bisphenol A with 2 mol of glycidyl (meth)acrylate (where it is methacrylate: GMA) (where the addition reaction product is methacrylate: Bis-GMA). The above polymerizable monomers may be used alone or in combination.

It should be understood that the explanations already given with regard to the polymerization initiator for the curable composition can be applied to the polymerization initiator in the same manner as with the above component (c).

In the tooth surface treating agent of the present invention, on the basis of the total amount of the components (a), (f), (g) and (c), preferably, the amount of the component (a) is 0.1 to 30% by weight, the amount of the component (f) is 70 to 99.9% by weight, the amount of the component (g) is 0 to 30% by weight, and the amount of the component (c) is 0 to 20 % by weight. More preferably, the amount of the component (a) is 1 to 20% by weight, the amount of the component (f) is 50 to 97.95% by weight, the amount of the component (c) is 0.05 to 15% by weight, and the amount of the component (g) is 1 to 15% by weight.

In the tooth surface treating agent of the present invention, the above components (a), (f), (g) and (c) may be mixed in advance and applied to a tooth. When a mixture of the above components may change in form and performance to impair the effects of the present invention because of storing it for a long period of time, each component may be separately stored, or these components may be divided to combinations as required, and stored, and these components may be mixed before use to prepare the tooth surface treating agent.

The method for storing the tooth surface treating agent includes a method in which the above components are divided into two groups such as a mixture of the components (a/f/g) and the component (c) and a method in which the above components are divided into a mixture of the components (a/f/g) and a mixture of the components (f/c). The method of dividing the components shall not be limited to the above combinations. These mixtures may be placed in separate containers and prepared as a kit for providing them as a commercial product. The tooth surface treating agent of the present invention is applied to a tooth surface and then a dental restorative resin and/or a tooth-bonding curable composition are/is applied thereon, whereby the dental restoration can be advantageously conducted.

When the tooth surface treating agent of the present invention and the curable composition of the present invention are used in combination, there is provided a method of treating a tooth surface, which comprises applying the tooth surface treating agent of the present invention to a tooth surface and then applying the curable composition of the present invention.

The above method of treating a tooth surface is preferably carried out in any one of the following two embodiments.

In the first preferred embodiment, the method of treating a tooth surface comprises applying a primer composition comprising (a') 1 to 30% by weight of at least one member selected from 4-(meth)acryloyloxyethyltrimellitic acid or an anhydride thereof and N-(meth)acryloylaminosalicylic acid, (f') 30 to 90% by weight of at least one member selected from the group consisting of an aqueous ethanol or an aqueous acetone, (g') 1 to 20% by weight of a (meth)acrylate having an oxyalkylene group, and (c') 1 to 20% by weight of an aromatic sulfinate to a tooth surface, and applying a visible light-curable composition comprising (a') 1 to 30% by weight of at least one member selected from 4-(meth)acryloyloxyethyltrimellitic acid or an anhydride thereof and N-(meth)acryloylaminosalicylic acid, (b') 30 to 90% by weight of at least one member selected from the group consisting of 2-hydroxyethyl (meth)acrylate, 2-hydroxypropyl (meth)acrylate, glycerol (meth)acrylate, erythritol (meth)acrylate and poly-(meth)acrylate of an polyepoxy compound of bisphenol, (c') 0.1 to 5% by weight of a combination of d,l-camphorquinone which is a visible light sensitizer and at least one reducing agent selected from N-phenylglycine, N,N-dialkylaminobenzoic acid and aromatic sulfinate, and (d') 3 to 20% by weight of a (meth)acrylate having an oxyalkylene group in its molecule, and having a viscosity in the range of from 100 to 30,000 cp when measured at 37.5° C.

In the second preferred embodiment, the method of treating a tooth surface comprises applying a primer composition comprising (a') 1 to 30% by weight of at least one member selected from 4-(meth)acryloyloxyethyltrimellitic acid or an anhydride thereof and N-(meth)acryloylaminosalicylic acid, (f') 30 to 90% by weight of at least one member selected from the group consisting of an aqueous ethanol or an aqueous acetone, and (g') 1 to 20% by weight of a (meth)acrylate having an oxyalkylene group, and applying a room temperature curable composition comprising (a') 1 to 30% by weight of at least one member selected from 4-(meth)acryloyloxyethyltrimellitic acid or an anhydride thereof and N-(meth)acryloylaminosalicylic acid, (b') 10 to 60% by weight of at least one member selected from the group consisting of 2-hydroxyethyl (meth)acrylate, 2-hydroxypropyl (meth)acrylate, glycerol (meth)acrylate, erythritol (meth)acrylate and poly-(meth)acrylate of an polyepoxy compound of bisphenol, (c') 0.1 to 10% by weight of a combination of at least one member selected from d,l-camphorquinone, an organic peroxide and an inorganic peroxide with at least one reducing agent selected from N-phenylglycine, N,N-dimethyl-p-toluidine, N,N-diethanol-p-toluidine, N,N-dialkylaminobenzoic acid and aromatic sulfinate, (d') 10 to 60% by weight of a (meth)acrylate having an oxyalkylene group in its molecule, and (e') a filler containing any one of 10 to 60 % by weight of a zirconium oxide filler having an average particle diameter of 0.05 to 10 μm, 5 to 80% by weight of a spherical silica filler having an average particle diameter of 1 to 10 μm and 5 to 30% by weight of an organic composite filler having an average particle diameter of 1 to 30 μm.

The present invention will be detailed hereinafter with reference to Examples.

In the evaluation of adhesion strength, a curable composition was prepared as a bonding material for a composite resin or as a resin cement and evaluated as follows.

Fresh bovine lower-jaw anterior teeth, which had been taken out, frozen in water and stored, were used as tooth samples. A thawed bovine tooth was ground with a rotary grinder ECOMET-III (supplied by BUEHLER) with pouring water under manual pressure up to a water-resistant emery paper #600 so that the enamel and dentin were exposed, whereby a smooth surface was prepared. Water was removed from the grounded bovine tooth with an air gun. Immediately thereafter, a Cellophane tape having a hole having a diameter of 5.1 mm was attached to the bovine tooth to define an adhesion area, and the bovine tooth was again immersed in water.

The bovine tooth was allowed to stand in the water for at least 1 minute, and then taken out. Water was lightly wiped off from the adhesion surface with a ball of cotton. The adhesion surface still had some water, and was used as a wet surface for an adhesion test.

(1) Application as Bonding Material for Composite Resin

A curable composition was applied to a sponge (accessory to Super Bond C&B, supplied by Sun Medical Co., Ltd), and moderately exposed to air blowing from an air gun for about 5 seconds. The curable composition was exposed to visible light from a visible light irradiation apparatus (Translux CL, Kulzer) for 20 seconds to cure the composition. A cardboard with a ring hole having an internal diameter of 5.1 mm and a depth of 1 mm and having an adhesive on one surface was placed and fixed, and this hole was filled with a composite resin (Silux Plus, 3M), and coated with a polyester film having a thickness of 50 μm. The composite resin was exposed through this film to visible light from a visible light irradiation apparatus (Translux CL, Kulzer) for 40 seconds to cure the composite resin, and the film was peeled off. An acryl rod was planted upright with METAFAST (supplied by Sun Medical Co., Ltd) and allowed to stand for 15 minutes.

(2) Application as Resin Cement

Liquid component(s) and powder component(s) separately stored for the third curable composition of the present invention were mixed in a Dappen glass just before use or fully kneaded on kneading paper. Then, the resultant mixture was applied to the defined adhesion surface, and an acryl rod was planted upright and allowed to stand for 15 minutes.

The sample prepared by the above method (1) or (2) was immersed in water at 37° C. for 24 hours, and then subjected to a tension adhesion test (cross head speed 2 mm/min.).

The interface between the tooth and the composite resin was measured for a gap by the following method, while this measurement was not carried out when the resin cement was used.

For determining the full contact between a tooth and a restorative material, a thawed bovine tooth was ground with a rotary grinder ECOMET-III (supplied by BUEHLER) with pouring water under manual pressure up to a water-resistant emery paper #600 so that the enamel and dentin were exposed, whereby a smooth surface was prepared. A $\phi 3\times 3$ mm cavity was formed with a diamond point with pouring water. A curable composition of the present invention was applied to a surface of the cavity with a sponge, exposed to moderate air blowing with an air gun, and exposed to visible light from a visible light irradiation apparatus (Translux CL, Kulzer) for 20 seconds to cure the composition. Further, a composite resin was filled in the cavity, and similarly exposed to visible light for 40 seconds to cure the composite resin. The surface was made smooth by grinding the surface up to #600 with pouring water, and then, the bovine tooth was immersed in a basic fuchsin aqueous solution for 1 minute and washed with water. The bovine tooth was dried with an air gun and measured for a gap with an optical microscope, and the coloring in a portion where the gap was formed was visually observed to determine the formation of the gap.

For the viscosity of a curable composition, 1.0 cc of the curable composition was measured with a viscometer TYPE-EHD (TOKIMEC Co., Ltd) at 37.5° C.

EXAMPLE 1

A curable composition as a bonding material for a composite resin was prepared as follows. A solution containing 58.5 parts by weight of 2-hydroxyethyl methacrylate (HEMA), 35 parts by weight of VR90 (Showa Kobunshi K.K.), 6.5 parts by weight of 4-MET and 0.5 part by weight of d,l-camphorquinone (CQ) was prepared, and placed in a shaded dropping bottle. Separately, 0.3 part by weight of sponge chips S ($\phi 2\times 3$ mm) as an accessory to Superbond D Liner Plus and 0.5 part by weight of N-phenylglycine (NPG) were placed in a polyethylene bag and fully shaken to allow the sponge chips to contain NPG. One drop of the solution was taken from the dropping bottle onto a Dappen dish, and the solution was infiltrated into one sponge chip containing NPG and applied to a tooth surface. The composition was tested for adhesion to show that the adhesion strength to a dentin was $76\pm 38$ kgf/cm$^2$, and no formation of a gap was observed.

When the monomer components and NPG as the polymerization initiator component were divided as above, the curable composition of the present invention was storable for a long period of time without any change in form. Further, the adhesion procedures were simple and the time required for these procedures was decreased as compared with a conventional method in which components were divided and stored and they were mixed just before use and then applied.

EXAMPLE 2

A curable composition as a bonding material for a composite resin was prepared as follows. 45.5 Parts by weight of HEMA, 35 parts by weight of VR90, 6.5 parts by weight of triethylene glycol dimethacrylate (3G), 6.5 parts by weight of 2,2-bis(4-methacryloyloxypolyethoxyphenyl)propane (2.6E, Shin-Nakamura Kagaku K.K.), 6.5 parts by weight of 4-MET, 0.5 part by weight of CQ and 0.5 part by weight of NPG were mixed mixed to prepare solution. As soon as the solution was prepared, the solution was tested for adhesion to show that the adhesion strength to dentin was $99\pm 49$ kgf/cm$^2$, and no formation of a gap was observed. The solution containing NPG gelled about 1 day after being prepared, and was no longer usable.

EXAMPLE 3

A curable composition as a bonding material for a composite resin was prepared as follows. 52.5 Parts by weight of HEMA, 12.5 parts by weight of VR90, 7.5 parts by weight of 3G, 7.5 parts by weight of 2.6E, 7.5 parts by weight of 4-MET, 12.5 parts by weight of polyvinyl acetate (PVAc), 0.5 part by weight of CQ and 0.5 part by weight of NPG were mixed to prepare solution. As soon as the solution was prepared, the solution was tested for adhesion to show that the adhesion strength to dentin was $77\pm 18$ kgf/cm$^2$ and no formation of a gap was observed.

EXAMPLE 4

A curable composition was obtained in the same manner as in Example 2 except that 4-MET was replaced with 4-META (the composition had a viscosity of 280 cP). The curable composition showed that the adhesion strength to dentin was $78\pm 18$ kgf/cm$^2$, and no formation of a gap was observed.

EXAMPLE 5

A curable composition as a resin cement was a combination of the following liquid and powder components. A liquid component: 60 parts by weight of HEMA, 30 parts by weight of 2-hydroxy-3-phenoxypropyl methacrylate (HPPM), 4 parts by weight of 4-MET, 5 parts by weight of N-methacryloyl 5-aminosalicylic acid (5-MASA) and 1 part by weight of benzoyl peroxide (BPO). A powder component: 60 parts by weight of a zirconium oxide filler (ZrO$_2$, average particle diameter 2 µm) coated with 10% by weight of PMMA, 20 parts by weight of a spherical silica filler (SiO$_2$) having an average particle diameter of 5 µm, 20 parts by weight of an organic composite filler (TMPT.f) having an average particle diameter of 20 µm, prepared by coating a silica filler having an average particle diameter of 0.04 µm with trimethylolpropane trimethacrylate (TMPT) by preliminary polymerization and milling the resultant polymer, and 2 parts by weight of NPG. 0.09 Parts by weight of the liquid component and 0.13 part by weight of the powder component was mixed and kneaded on a kneading paper sheet, and 1 minute after the kneading, the mixture (curable composition) was used for an adhesion test. The composition showed that the adhesion strength to dentin was $57\pm 22$ kgf/cm$^2$.

EXAMPLE 6

A curable composition was prepared in the same manner as in Example 5 except that HPPM for a liquid component was replaced with TMPT. The composition showed that the adhesion strength to dentin was $42\pm 20$ kgf/cm$^2$.

EXAMPLE 7

A curable composition was prepared in the same manner as in Example 5 except that HPPM for a liquid component was replaced with an adduct (UDMA) of 1 mol of 2,2,4-trimethylhexamethylene diisocyanate with 2 mol of HEMA. The composition showed that the adhesion strength to dentin was 69±25 kgf/cm$^2$.

EXAMPLE 8

A curable composition was prepared in the same manner as in Example 5 except that HPPM for a liquid component was replaced with VR90. The composition showed that the adhesion strength to dentin was 40±8 kgf/cm$^2$.

EXAMPLE 9

A curable composition was prepared in the same manner as in Example 5 except that HPPM for a liquid Component was replaced with 3G and that the amount of NPG for a powder component was changed to 1 part by weight. The composition showed that the adhesion strength to dentin was 50±9 kgf/cm$^2$.

EXAMPLE 10

A dentin surface was etched with a 10 wt % citric acid aqueous solution containing 3 wt % ferric chloride and washed with water. Then, water was removed with a ball of cotton, and the same curable composition as that prepared in Example 9 was applied to the dentin surface and tested in the same manner as in Example 9. The composition showed that the adhesion strength to dentin was remarkably high, as high as 107±15 kgf/cm$^2$.

A primer of the present invention was applied to all area-defined surface with a sponge (accessory to Super bond C&B, supplied by Sun Medical), and allowed to stand for 30 seconds. Superfluous liquid was removed by blowing air to the surface for about 5 seconds to prepare a treated surface. This treated surface was bonded using the curable composition prepared in Example 2 or 9.

The curable composition obtained in Example 2 was used as a bonding material for a composite resin for the adhesion test, and the curable composition obtained in Example 9 was used as a resin cement for the adhesion test.

The opened state of dental tubules was observed in the following procedures. That is, in the method of evaluation of adhesion, a tooth surface treating agent was applied to a ground dentin surface and superfluous liquid was removed by blowing air. Thereafter, the dentin surface was observed through an optical microscope to see the open state of the dental tubules.

EXAMPLE 11

A solution containing 20 parts by weight of 4-MET and 80 parts by weight of ethanol (EtOH) was used as a tooth surface treating agent, and the same curable composition as that obtained in Example 2 was used and adhesion strengths to enamel and to dentin were measured. As a result, the composition showed that the adhesion strength to enamel was 65±8 kgf/cm$^2$ and that the adhesion strength to dentin was 73±15 kgf/cm$^2$. When the dental tubules were observed through an optical microscope after the dentin was treated, no opening of the tubules was observed. Further, no formation of a gap was found.

EXAMPLE 12

A solution containing 20 parts by weight of 4-MET, 20 parts by weight of distilled water (H$_2$O) and 80 parts by weight of EtOH was used as a tooth surface treating agent, and the same curable composition as that obtained in Example 2 was used, and adhesion strengths to enamel and to dentin were measured. As a result, the composition showed that the adhesion strength to enamel was 96±20

TABLE 1

| Ex. No. | Curable composition (parts by weight) | | | | | Viscosity (cP) | Adhesion strength (kgf/cm$^2$) | GAP |
|---|---|---|---|---|---|---|---|---|
| | A | B | C | D | E | | | |
| 1 | 4-MET | HEMA VR90 | CQ NPG | — | — | 180 | 76 ± 88 | No |
| 2 | 4-MET | HEMA VR90 | CQ NPG | 3G 2.6E | — | 230 | 99 ± 49 | No |
| 3 | 4-MET | HEMA VR90 | CQ NPG | 3G 2.6E | PVAc | 860 | 77 ± 18 | No |
| 4 | 4-META | HEMA VR90 | CQ NPG | 3G 2.6E | — | 280 | 78 ± 18 | No |
| 5 | 4-MET 5-MASA | HEMA HPPM | BPO NPG | — | ZrO$_2$ SiO$_2$ TMPT.f | 5300 | 57 ± 22 | — |
| 6 | 4-MET 5-MASA | HEMA | BPO NPG | TMPT | ZrO$_2$ SiO$_2$ TMPT.f | 7800 | 42 ± 20 | — |
| 7 | 4-MET 5-MESA | HEMA VR90 | BPO NPG | UDMA | ZrO$_2$ SiO$_2$ TMPT.f | 7000 | 69 ± 25 | — |
| 8 | 4-MET 5-MASA | HEMA VR90 | BPO NPG | — | ZrO$_2$ SiO$_2$ TMPT.F | 9500 | 40 ± 8 | — |
| 9 | 4-MET 5-MASA | HEMA | BPO NPG | 3G | ZrO$_2$ SiO$_2$ TMPT.f | 7200 | 50 ± 9 | — |
| 10 | 4-MET 5-MASA | HEMA | BPO NPG | 3G | ZrO$_2$ SiO$_2$ TMPT.f | 7900 | 107 ± 15 (etching) | — | kgf/cm² and that the adhesion strength to dentin was 101±20 kgf/cm². When the dental tubules were observed through an optical microscope after the dentin was treated, no opening of the tubules was observed. Further, no formation of a gap was found.

EXAMPLE 13

A solution containing 15 parts by weight of 4-MET, 6 parts by weight of N-methacryloyl-5-aminosalicylic acid (5-MASA), 20 parts by weight of H₂O and 80 parts by weight of EtOH was used as a tooth surface treating agent, and the same curable composition as that obtained in Example 2 was used, and adhesion strengths to enamel and to dentin were measured. As a result, the composition showed that the adhesion strength to enamel was 64±24 kgf/cm² and that the adhesion strength to dentin was 90±28 kgf/cm². When the dental tubules were observed through an optical microscope after the dentin was treated, no opening of the tubules was observed. Further, no formation of a gap was found.

EXAMPLE 14

A solution containing 20 parts by weight of 4-MET, 42.5 parts by weight of H₂O and 37.5 parts by weight of EtOH was used as a tooth surface treating agent, and the same curable composition as that obtained in Example 2 was used, and adhesion strengths to enamel and to dentin were measured. As a result, the composition showed that the adhesion strength to enamel was 93±18 kgf/cm² and that the adhesion strength to dentin was 111±23 kgf/cm². When the dental tubules were observed through an optical microscope after the dentin was treated, no opening of the tubules was observed. Further, no formation of a gap was found.

EXAMPLE 15

A solution containing 10 parts by weight of 4-MET, 40 parts by weight of EtOH, 45 parts by weight of H₂O and 5 parts by weight of nonaethylene glycol dimethacrylate (9G) was used as a tooth surface treating agent, and the same curable composition as that obtained in Example 2 was used, and adhesion strengths to enamel and to dentin were measured. As a result, the composition showed that the adhesion strength to enamel was 70±12 kgf/cm² and that the adhesion strength to dentin was 83±7 kgf/cm². When the dental tubules were observed through an optical microscope after the dentin was treated, no opening of the tubules was observed. Further, no formation of a gap was found.

EXAMPLE 16

A solution containing 10 parts by weight of 4-MET, 40 parts by weight of EtOH, 45 parts by weight of H₂O and 5 parts by weight of polyethylene glycol dimethacrylate (23G) was used as a tooth surface treating agent, and the same curable composition as that obtained in Example 9 was used, and adhesion strengths to enamel and to dentin were measured. As a result, the composition showed that the adhesion strength to enamel was 102±18 kgf/cm² and that the adhesion strength to dentin was 109±33 kgf/cm². When the dental tubules were observed through an optical microscope after the dentin was treated, no opening of the tubules was observed.

EXAMPLE 17

A solution containing 10 parts by weight of 4-META, 5 parts by weight of 5-MASA, 40 parts by weight of EtOH, 40 parts by weight of H₂O and 5 parts by weight of 23G was used as a tooth surface treating agent, and the same curable composition as that obtained in Example 9 was used, and adhesion strengths to enamel and to dentin measured. As a result, the composition showed that the adhesion strength to enamel was 108±32 kgf/cm² and that the adhesion strength to dentin was 110±37 kgf/cm². When the dental tubules were observed through an optical microscope after the dentin was treated, no opening of the tubules was observed.

EXAMPLE 18

A solution containing 20 parts by weight of 4-MET, 20 parts by weight of EtOH, 70 parts by weight of H₂O and 0.05 part by weight of CQ was used as a tooth surface treating agent, and the same curable composition as that obtained in Example 2 was used, and adhesion strengths to enamel and to dentin were measured. As a result, the composition showed that the adhesion strength to enamel was 51±26 kgf/cm² and that the adhesion strength to dentin was 62±18 kgf/cm². When the dental tubules were observed through an optical microscope after the dentin was treated, no opening of the tubules was observed. Further, no formation of a gap was found.

EXAMPLE 19

A solution containing 5 parts by weight of 4-MET, 45 parts by weight of EtOH, 48 parts by weight of H₂O, 2 parts by weight of 3G, 0.05 part by weight of CQ and 0.1 part by weight of N,N.-dimethylaminobenzoic acid (DEABA) was used as a tooth surface treating agent, and the same curable composition as that obtained in Example 2 was used, and adhesion strengths to enamel and to dentin were measured. As a result, the composition showed that the adhesion strength to enamel was 44±14 kgf/cm² and that the adhesion strength to dentin was 51±14 kgf/cm². When the dental tubules were observed through an optical microscope after the dentin was treated, no opening of the tubules was observed. Further, no formation of a gap was found.

EXAMPLE 20

A solution containing 10 parts by weight of 4-MET, 40 parts by weight of EtOH, 45 parts by weight of H₂O, 5 parts by weight of nonaethylene glycol dimethacrylate (9G) and 0.05 part by weight of CQ was used as a tooth surface treating agent, and the same curable composition as that obtained in Example 2 was used, and adhesion strengths to enamel and to dentin were measured. As a result, the composition showed that the adhesion strength to enamel was 93±8 kgf/cm² and that the adhesion strength to dentin was 113±13 kgf/cm². When the dental tubules were observed through an optical microscope after the dentin was treated, no opening of the tubules was observed. Further, no formation of a gap was found.

EXAMPLE 21

A solution containing 10 parts by weight of 4-MET, 40 parts by weight of EtOH, 45 parts by weight of H₂O, 5 parts by weight of 9G, 0.05 part by weight of CQ and 5 part by weight of NPG was used as a tooth surface treating agent, and the same curable composition as that obtained in Example 2 was measured for adhesion strength to enamel and dentin. As a result, the composition showed that the adhesion strength to enamel was 70±10 kgf/cm² and that the adhesion strength to dentin was 87±21 kgf/cm². When the dental tubules were observed through an optical microscope after the dentin was treated, no opening of the tubules was observed. Further, no formation of a gap was found.

EXAMPLE 22

A solution containing 10 parts by weight of 4-MET, 40 parts by weight of EtOH, 45 parts by weight of H₂O, 5 parts by weight of 9G and 0.05 part by weight of CQ was used as a tooth surface treating agent, and the same curable composition as that obtained in Example 2 was used, and adhesion strengths to enamel and to dentin were measured. As a result, the composition showed that the adhesion strength to enamel was 89±15 kgf/cm² and that the adhesion strength to dentin was 99±11 kgf/cm². When the dental tubules were observed through an optical microscope after the dentin was treated, no opening of the tubules was observed through an optical microscope after the dentin was treated, no opening of the tubules was observed.

EXAMPLE 24

A solution containing 20 parts by weight of 4-META, 60 parts by weight of EtOH, 15 parts by weight of H₂O and 4 parts by weight of 23G, and a solution containing 5 parts by weight of sodium p-toluenesulfinate (pTSNa), 10 parts by weight of EtOH, 80 parts by weight of H₂O and 5 parts by weight of 23G were mixed in equal amounts just before use. The resultant mixture was used as a tooth surface treating agent, and the same curable composition as that obtained in Example 2 was used, and adhesion strengths to enamel and to dentin were measured. As a result, the composition showed that the adhesion strength to enamel was 129±27 kgf/cm² and that the adhesion strength to dentin was 128±16 kgf/cm². When the dental tubules were observed through an optical microscope after the dentin was treated, no opening of the tubules was observed. Further, no formation of a gap was found.

TABLE 2

| Ex. No. | Primer composition (parts by weight) | | | | Curable composition | Opening of dental tubules | Adhesion strength (kgf/cm³) | GAP |
|---|---|---|---|---|---|---|---|---|
| | F | G | H | J | | | | |
| 11 | 4-MET | ETOH | — | — | Example 2 | No | E: 65 ± 8<br>D: 73 ± 15 | No |
| 12 | 4-MET | H₂O<br>EtOH | — | — | Example 2 | No | E: 96 ± 20<br>D: 101 ± 20 | No |
| 13 | 4-MET<br>5-MASA | H₂O<br>ETOH | — | — | Example 2 | No | E: 64 ± 24<br>D: 90 ± 28 | No |
| 14 | 4-META | H₂O<br>EtOH | — | — | Example 2 | No | E: 93 ± 18<br>D: 111 ± 23 | No |
| 15 | 4-MET | H₂O<br>EtOH | 9G | — | Example 2 | No | E: 70 ± 12<br>D: 83 ± 7 | No |
| 16 | 4-MET | H₂O<br>ETOH | 23G | — | Example 9 | No | E: 102 ± 18<br>D: 109 ± 33 | — |
| 17 | 4-META | H₂O<br>EtOH | 23G | — | Example 9 | No | E: 108 ± 32<br>D: 110 ± 37 | — |
| 18 | 4-MET | H₂O<br>EtOH | — | CQ | Example 2 | No | E: 51 ± 26<br>D: 62 ± 18 | No |
| 19 | 4-MET | H₂O<br>EtOH | 3G | CQ<br>DEABA | Example 2 | No | E: 44 ± 14<br>D: 51 ± 14 | No |
| 20 | 4-MET | H₂O<br>ETOH | 9G | CQ | Example 2 | No | E: 93 ± 8<br>D: 113 ± 13 | No |
| 21 | 4-MET | H₂O<br>ETOH | 9G | CQ<br>NPG | Example 2 | No | E: 70 ± 10<br>D: 87 ± 21 | No |
| 22 | 4-META | H₂O<br>ETOH | 9G | CQ | Example 2 | No | E: 89 ± 15<br>D: 99 ± 11 | No |
| 23 | 4-MET | H₂O<br>EtOH | — | BSNa | Example 9 | No | E: 118 ± 38<br>D: 115 ± 19 | No |
| 24 | 4-MET<br>5-MASA | H₂O<br>ETOH | 23G | pTSNa | Example 2 | No | E: 129 ± 27<br>D: 128 ± 16 | No | observed. Further, no formation of a gap was found.

EXAMPLE 23

A solution containing 20 parts by weight of 4-MET, 65 parts by weight of EtOH and 15 parts by weight of H₂O, and a solution containing 85 parts by weight of H₂O, 10 parts by weight of EtOH and 5 parts by weight of sodium benzenesulfinate (BSNa) were mixed in equal amounts just before use. The resultant mixture was used as a tooth surface treating agent, and the same curable composition as that obtained in Example 9 was used, and adhesion strengths to enamel and to dentin were measured. As a result, the composition showed that the adhesion strength to enamel was 118±38 kgf/cm² and that the adhesion strength to dentin was 115±19 kgf/cm². When the dental tubules were

COMPARATIVE EXAMPLE 1

A curable composition as a bonding material for a composite resin was prepared in the same manner as in Example 1 except that HEMA and VR90 were replaced with methyl methacrylate (MMA) and UDMA. As a result, while a test sample was immersed in water, it was peeled off.

COMPARATIVE EXAMPLE 2

A curable composition as a bonding material for a composite resin was prepared in the same manner as in Example 3 except that HEMA and VR90 were replaced with MMA and UDMA (viscosity; 230 cP). As a result, while a test sample was immersed in water, it was peeled off.

COMPARATIVE EXAMPLE 3

A curable composition as a bonding material for a composite resin was prepared in the same manner as in Example 3 except that a solution (viscosity: 230 cP) containing neither CQ nor NPG as a polymerization initiator (c) component was used. As a result, while a test sample was immersed in water, it was peeled off.

COMPARATIVE EXAMPLE 4

A curable composition as a bonding material for a composite resin was prepared in the same manner as in Example 3 except That a solution (viscosity: 230 cP) containing no polymerizable monomer (a) component having an acidic group in its molecule was used. As a result, no formation of a gap was found, while the adhesion strength to dentin was very low, as low as 23±13 kgf/cm$^2$.

COMPARATIVE EXAMPLE 5

A curable composition as a resin cement was prepared in the same manner as in Example 5 except that HEMA and HPPM as the polymerizable monomer (b) component containing a hydroxyl group in its molecule were replaced with UDMA. As a result, while a test sample was immersed in water, it was peeled off.

COMPARATIVE EXAMPLE 6

A curable composition as a resin cement was prepared in the same manner as in Example 6 except that no polymerization initiator (c) component was used, and the curable composition was tested for adhesion. As a result, the curable composition did not undergo curing, and while a test sample was immersed in water, it was peeled off.

COMPARATIVE EXAMPLE 7

A curable composition as a resin cement was prepared in the same manner as in Example 9 except that no polymerizable monomer (a) component containing an acidic group in its molecule was used, and the curable composition was tested for adhesion. As a result, the composition showed that the adhesion strength to dentin was low, as low as 38±21 kgf/cm$^2$.

COMPARATIVE EXAMPLE 8

An adhesion test was carried out in the same manner as in Example 11 except that 4-MET as a polymerizable monomer containing an acidic group in its molecule was omitted from the tooth surface treating agent. As a result, while a test sample for adhesion to enamel was immersed in water, it was peeled off. The adhesion strength to dentin was 20±8 kgf/cm$^2$, or much lower than that in Example 11. The formation of a gap was found.

COMPARATIVE EXAMPLE 9

A composition was prepared in the same manner as in Example 11 except that EtOH as an organic solvent was omitted from the tooth surface treating agent. In this case, 4-MET was not dissolved since it was a solid, and no adhesion test was carried out.

COMPARATIVE EXAMPLE 10

A composition was prepared in the same manner as in Example 15 except that EtOH as an organic solvent was omitted from the tooth surface treating agent. In this case, 4-MET was not dissolved since it was a solid, and no adhesion test was carried out.

COMPARATIVE EXAMPLE 11

An adhesion test was carried out in the same manner as in Example 11 except that the tooth surface treating agent was replaced with a commercially available total etching agent and that the applied total etching agent was not washed with water but air-dried. A tooth surface treating agent (Green) belonging to Super bond C&B (Sum Medical Co., Ltd) was used as the above total etching agent. As a result, when dental tubules were observed through an optical microscope after the treatment to dentin, all the dental tubules were opened. Further, while a test sample Was immersed in water, rods bonded to enamel and dentin were all peeled off, or not at all bonded.

TABLE 3

| Comp. Ex. No. | Curable composition (parts by weight) | | | | | Viscosity (cP) | Adhesion strength (kgf/cm$^2$) | GAP |
|---|---|---|---|---|---|---|---|---|
| | A | B | C | D | E | | | |
| 1 | 4-MET | — | CQ NPG | MMA UDMA | — | 120 | 0 | yes |
| 2 | 4-MET | — | CQ NPG | 3G 2.6E MMA UDMA | PVAc | 230 | 0 | yes |
| 3 | 4-MET | HEMA VR90 | — | 3G 2.6E | PVAc | 230 | 0 | yes |
| 4 | — | HEMA VR90 | CQ NPG | 9G 2.6E | PVAc | 230 | 23 ± 13 | No |
| 5 | 4-MET 5-MASA | — | BPO NPG | UDMA | ZrO$_2$ SiO$_2$ TMPT.f | 7900 | 0 | — |
| 6 | 4-MET 5-MASA | HEMA | — | TMPT | ZrO$_2$ SiO$_2$ TMPT.f | 7600 | Not cured | — |
| 7 | — | HEMA | BPO NPG | 3G | ZrO$_2$ SiO$_2$ TMPT.f | 7700 | 38 ± 21 | — |

COMPARATIVE EXAMPLE 12

An adhesion test was carried out in the same manner as in Example 11 except that the tooth surface treating agent was replaced with a primer belonging to a commercially available, Super bond D liner Plus (Sun Medical). As a result, the adhesion strength to enamel was as low as 48±21 kgf/cm², and the adhesion strength to dentin was as low as 53±19 kgf/cm². when dental tubules were observed through an optical microscope after the treatment, no opening of dental tubules was found, while the formation of a gap was found.

COMPARATIVE EXAMPLE 13

An adhesion test was carried out in the same manner as in Example 18 except that 4-MET as a polymerizable monomer containing an acidic group in its molecule was omitted from the tooth surface treating agent. As a result, while a test sample for adhesion to enamel was immersed in water, it was peeled off. The adhesion strength to dentin was 18±10 kgf/cm², or much lower than that in Example 18.

COMPARATIVE EXAMPLE 14

An attempt was made to prepare a solution as a tooth surface treating agent in the same manner as in Example 18 except that EtOH as an organic solvent was omitted from the composition shown in Example 18. In this case, the mixture underwent phase separation, and no solution was formed.

COMPARATIVE EXAMPLE 15

An adhesion test was carried out in the same manner as in Example 20 except that CQ as a polymerization initiator was omitted from the composition as a tooth surface treating agent shown in Example 20. As a result, the adhesion strength to enamel was 70±12 kgf/cm², and the adhesion strength to dentin was 83±7 kgf/cm², which values were low as compared with those in Example 20.

COMPARATIVE EXAMPLE 16

An adhesion test was carried out in the same manner as in Example 16 except that 4-MET as a polymerizable monomer containing an acidic group in its molecule was omitted from the tooth surface treating agent. As a result, while a test sample for adhesion to enamel was immersed in water, it was peeled off. The adhesion strength to dentin was 52±13 kgf/cm², or much lower than that in Example 16.

TABLE 4

| Comp. Ex. No. | Primer composition (parts by weight) | | | | Curable composition | Opening of dental tubules | Adhesion strength (kgf/cm³) | GAP |
|---|---|---|---|---|---|---|---|---|
| | F | G | H | J | | | | |
| 8 | — | ETOH | — | — | Example 2 | No | E: 0  D: 20 ± 8 | yes |
| 9 | 4-MET | — | — | — | Example 2 | — | Not usable | |
| 10 | 4-MET | — | 9G | — | Example 2 | — | Not dissolved | |
| 11 | | Super bond C & B Surface treating agent (not washed with water) | | | Example 2 | yes | E: 0  D: 0 | yes |
| 12 | | Super bond D liner plus primer | | | Example 2 | No | E: 48 ± 21  D: 53±19 | yes |
| 13 | — | H₂O EtOH | — | CQ | Example 2 | No | E: 0  D: 18 ± 10 | yes |
| 14 | 4-MET | — | — | CQ | — | — | Not dissoved | — |
| 15 | 4-MET | H₂O EtOH | 9G | — | Example 2 | No | E: 70 ± 12  D: 83 ± 7 | — |
| 16 | — | H₂O EtOH | 23G | — | Example 9 | No | E: 0  D: 52 ± 13 | — |

What is claimed is:

1. A curable composition comprising (A3) (a) a polymerizable unsaturated monomer having an acidic group in its molecule, (b) a polymerizable unsaturated monomer having a hydroxyl group in its molecule, (c) a polymerization initiator, (c1) an amine compound of the formula (I)

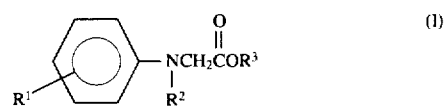

wherein each of $R^1$ and $R^2$ is independently a hydrogen atom or an alkyl group which may contain a functional group or a substituent, and $R_3$ is a hydrogen atom or a metal atom, (e) a combination of 40 to 80% by weight of a zirconium oxide filler having an average particle diameter of 0.05 to 10 μm and 10 to 30% by weight of an organic composite filler having an average particle diameter of 1 to 30 μm, wherein;

on the basis of a total amount of components (a), (b) and (c), the amount of the component (a) is 1 to 50% by weight, the amount of the component (b) is 1 to 98.99% by weight, and the amount of the component (c) is 0.01 to 50% by weight, and on the basis of a total amount of components (a), (b), (c) and (e), the amount of the component (e) is 15 to 85% by weight, (B1) the curable composition having a viscosity in the range of from 100 to 30,000 cp when measured at 37.5° C.

2. A curable composition comprising (A4) (a) a polymerizable unsaturated monomer having an acidic group in its molecule, (b) a polymerizable unsaturated monomer having a hydroxyl group in its molecule, (c) a polymerization initiator, (c1) an amine compound of the formula (I)

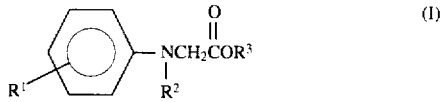

wherein each of $R^1$ and $R^2$ is independently a hydrogen atom or an alkyl group which may contain a functional group or a substituent, and $R^3$ is a hydrogen atom or metal atom, (d) other polymerizable monomer copolymerizable with at least one of the above components (a) and (b), and (e) at least one member selected from the group consisting of an organic filler, an inorganic filler and an organic composite filler, said organic composite filler being a filler obtained by coating a fine silica powder or zirconium oxide with a polymerizable unsaturated monomer by polymerization and then milling the coated product, wherein;

on the basis of a total amount of components (a), (b) and (c), the amount of component (a) is 1 to 50% by weight, the amount of the component (b) is 1 to 98.99% by weight and the amount of component (c) is 0.01 to 50% by weight, on the basis of a total amount of components (a), (b), (c) and (d), the amount of component (d) is 3 to 50% by weight, and on the basis of a total amount of components (a), (b), (c), (d) and (e), the amount of component (e) is 15 to 85% by weight, (B1) the curable composition having a viscosity in the range of from 100 to 30,000 cp when measured at 37.5° C.

3. The composition of claim 2, wherein the component (e) is a combination of 40 to 80% by weight of a zirconium oxide filler having an average particle diameter of 0.05 to 10 µm, 10 to 30% by weight of a spherical silica filler having an average particle diameter of 1 to 10 µm and 10 to 30% by weight of an organic composite filler having an average particle diameter of 1 to 30 µm.

4. The composition of claim 3, wherein the amine compound of formula (I) is N-phenylglycine or N-tolylglycine.

\* \* \* \* \*

UNITED STATES PATENT AND TRADEMARK OFFICE
CERTIFICATE OF CORRECTION

PATENT NO. : 5,530,038
DATED : June 25, 1996
INVENTOR(S) : Takashi YAMAMOTO, et al.

It is certified that error appears in the above-indentified patent and that said Letters Patent is hereby corrected as shown below:

Column 26, line 52, following "to 10 μm" insert --, 10 to 30% by weight of a spherical silica filler having an average particle diameter of 1 to 10 μm--.

Signed and Sealed this

Tenth Day of December, 1996

Attest:

BRUCE LEHMAN

Attesting Officer

Commissioner of Patents and Trademarks